United States Patent
Haartsen et al.

(10) Patent No.: US 8,622,919 B2
(45) Date of Patent: Jan. 7, 2014

(54) APPARATUS, METHOD, AND COMPUTER PROGRAM FOR DETECTING A PHYSIOLOGICAL MEASUREMENT FROM A PHYSIOLOGICAL SOUND SIGNAL

(75) Inventors: Jacobus Cornelis Haartsen, Hardenberg (NL); Gerrit Sampimon, Erm (NL)

(73) Assignees: Sony Corporation, Tokyo (JP); Sony Mobile Communications AB, Lund (SE)

( * ) Notice: Subject to any disclaimer, the term of this patent is extended or adjusted under 35 U.S.C. 154(b) by 866 days.

(21) Appl. No.: 12/272,072

(22) Filed: Nov. 17, 2008

(65) Prior Publication Data

US 2010/0125218 A1    May 20, 2010

(51) Int. Cl.
*A61B 5/02* (2006.01)
*A61B 5/04* (2006.01)
*H04R 25/00* (2006.01)

(52) U.S. Cl.
USPC .......................... 600/528; 600/514; 381/375

(58) Field of Classification Search
USPC ............ 600/300, 528–529, 586; 381/56, 375; 128/903, 905; 482/148; 84/612; 484/148
See application file for complete search history.

(56) References Cited

U.S. PATENT DOCUMENTS

| | | | |
|---|---|---|---|
| 5,492,129 A * | 2/1996 | Greenberger | 600/528 |
| 2002/0091049 A1 | 7/2002 | Hisano et al. | |
| 2006/0064037 A1 | 3/2006 | Shalon et al. | |
| 2006/0107822 A1 | 5/2006 | Bowen | |
| 2008/0146890 A1 | 6/2008 | LeBoeuf et al. | |
| 2008/0171945 A1 * | 7/2008 | Dotter | 600/514 |
| 2009/0108082 A1 * | 4/2009 | Goldmann et al. | 236/49.1 |
| 2009/0149699 A1 * | 6/2009 | Ullmann | 600/28 |
| 2009/0259116 A1 * | 10/2009 | Wasserman et al. | 600/323 |
| 2010/0037753 A1 * | 2/2010 | Wagner | 84/612 |

FOREIGN PATENT DOCUMENTS

| | | |
|---|---|---|
| GB | 2 419 946 | 5/2006 |
| WO | 2006/050512 | 5/2006 |

OTHER PUBLICATIONS

International Search Report for corresponding application No. PCT/EP2009/056078 dated Nov. 12, 2009.
Written Opinion for corresponding application No. PCT/EP2009/056078 dated Nov. 12, 2009.

* cited by examiner

*Primary Examiner* — Christopher D Koharski
*Assistant Examiner* — Catherine Voorhees
(74) *Attorney, Agent, or Firm* — Renner, Otto, Boisselle & Sklar, LLP

(57) ABSTRACT

An apparatus is disclosed, comprising a speaker suitable to be applied at a user's ear and enabled to be supplied with an audio signal for rendering; a microphone arranged in vicinity of the speaker to acquire a sound signal from sounds present in the ear of the user; and a signal processor, wherein the signal processor is arranged to subtract the audio signal from the sound signal to provide a physiological sound signal, and the signal processor is further arranged to detect a physiological measurement from the physiological sound signal. A method and a computer program are also disclosed.

37 Claims, 2 Drawing Sheets

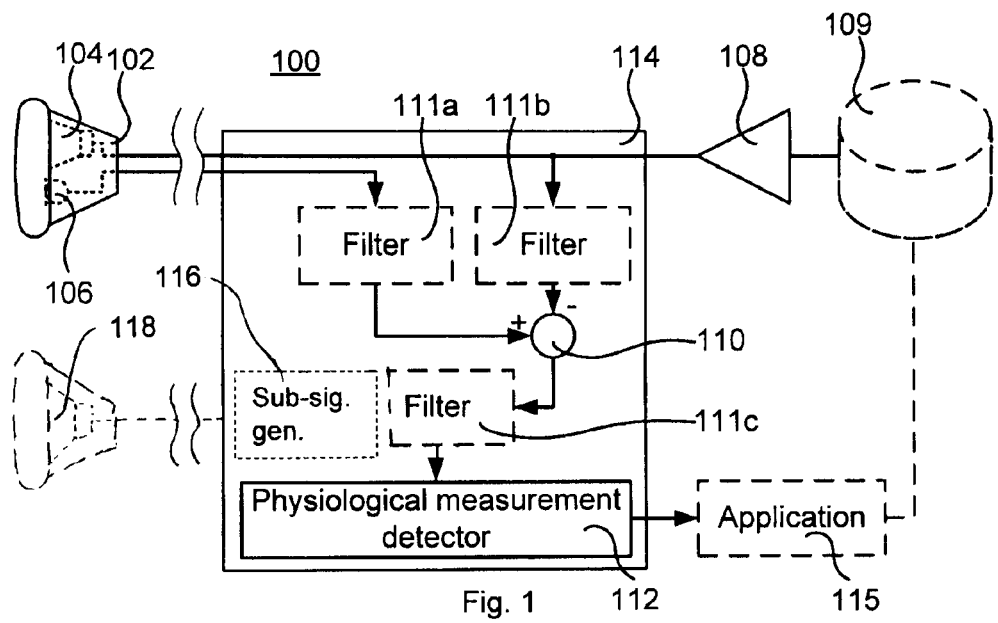
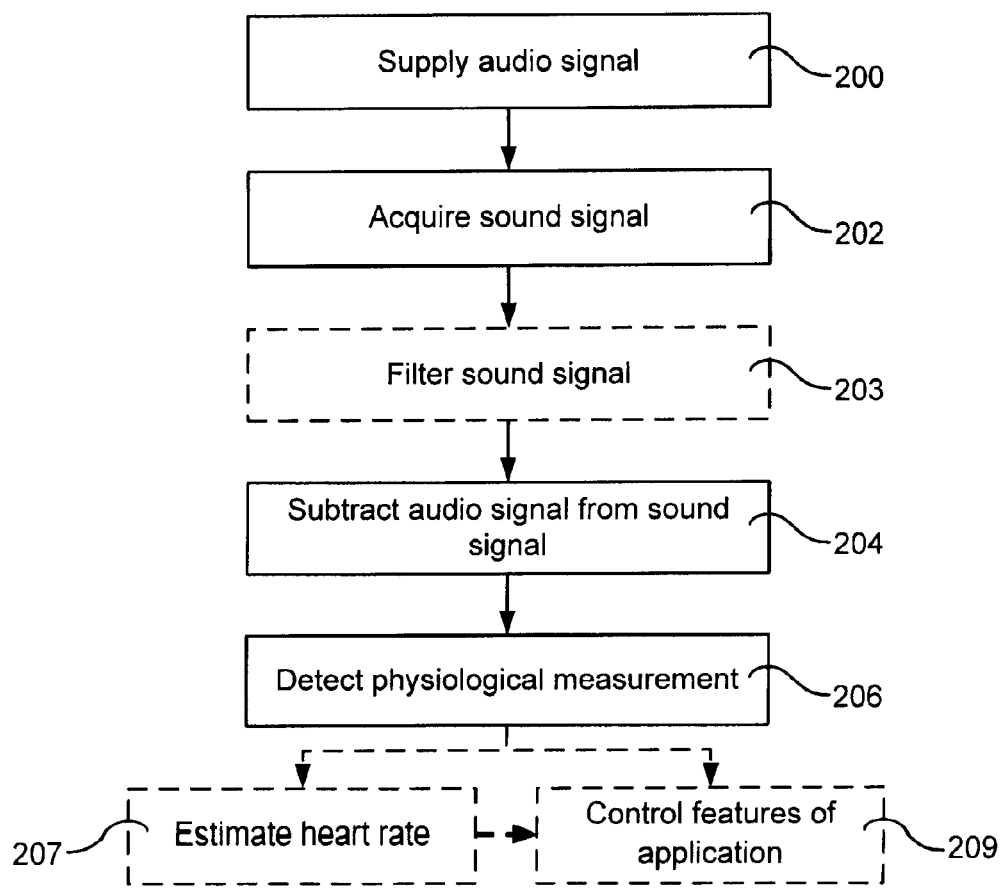

APPARATUS, METHOD, AND COMPUTER PROGRAM FOR DETECTING A PHYSIOLOGICAL MEASUREMENT FROM A PHYSIOLOGICAL SOUND SIGNAL

TECHNICAL FIELD

The present invention relates to an apparatus, a method, and a computer program for detecting a physiological measurement from a physiological sound signal.

BACKGROUND

Devices for exercising aid and applications in other devices for the same, or applications for other purposes, such as just for amusement have become popular. Such other devices can be portable media players, mobile telephones, and portable digital assistants. Positioning information means, accelerometers, altitude meters, etc. included in such devices may be used for added value. Applications for gaming, exercise aid, log functions, etc. may rely on these measured quantities.

Still, further measured quantities could enhance the devices. It is therefore a desire to add available quantities to measure. However, since the devices are intended to be used by an ordinary user without particular skills and the user normally appreciates gear that is easy to handle, sensors that are used for professional measurements are many times not suitable for these kinds of devices. It is therefore a further desire to provide gear that is easy to use by an ordinary user for the measurements.

SUMMARY

The present invention is based on the understanding that an ordinary user is comfortable with using earphones, and that addition of a microphone in an earphone can be used for acquiring sounds from which measurements on physiological sounds present in the user's ear can be made. The physiological sounds are extracted by subtracting sounds provided by the speaker of the earphone. From the physiological sounds, desired quantities and/or qualities are determined, such as heart rate or breathing pattern.

According to a first aspect, there is provided an apparatus comprising a speaker suitable to be applied at a user's ear and enabled to be supplied with an audio signal for rendering; a microphone arranged in vicinity of the speaker to acquire a sound signal from sounds present in the ear of the user; and a signal processor, wherein the signal processor is arranged to subtract the audio signal from the sound signal to provide a physiological sound signal, and the signal processor is further arranged to detect a physiological measurement from the physiological sound signal.

The apparatus may further comprise a filter arranged to filter the sound signal, the audio signal to be subtracted or the physiological sound signal.

The apparatus may further comprise an application arranged to control features of the application based on the physiological measurement. The application may be arranged to make music selection based on the physiological measurement, wherein the selected music is comprised in the supplied audio signal. The physiological measurement may comprise a breathing pattern. The signal processor may be arranged to determine a breathing rate from the breathing pattern. The music may be selected based on the music's beat rate such that the music's beat rate is a monotonic function of the breathing rate. The music may be selected based on the music's beat rate such that the music's beat rate is a function of the breathing rate wherein the music's beat rate is increased until a predetermined breathing rate is reached.

The physiological measurement may comprise a heartbeat. The signal processor may be arranged to determine a heartbeat rate from the heartbeat. The music may be selected based on the music's beat rate such that the music's beat rate is a monotonic function of the heartbeat rate. The music may be selected based on the music's beat rate such that the music's beat rate is a function of the heartbeat rate wherein the music's beat rate is increased until a predetermined heartbeat rate is reached. The signal processor may be arranged to extract the heartbeat by low pass filtering the physiological sound signal in a low pass filter to provide a heartbeat signal. The low pass filter may have a cutoff frequency between 3 and 10 Hz, preferably between 3 and 5 Hz, preferably 4 Hz.

The apparatus may further comprise a second speaker suitable to be provided at the user's other ear, wherein an audio signal provided to the second speaker comprises a sub-signal such that the sound signal comprises a signal component emanating from sound provided at the user's other ear and which sound is modulatedly attenuated by pulsating blood of veins of the user when the sound propagates through the head of the user, and such that the heartbeat is extractable from the signal component. The signal processor may be arranged to extract the heartbeat by low pass filtering the physiological sound signal in a low pass filter to provide the signal component signal. The low pass filter may have a cutoff frequency between 3 and 10 Hz, preferably between 3 and 5 Hz, preferably 4 Hz.

The apparatus may comprise a heart rate estimator arranged to estimate heart rate from the breathing pattern. The physiological measurement may comprise a heartbeat, the signal processor may be arranged to determine a heartbeat rate from the heartbeat, and the apparatus may further be arranged to provide a comparison between the estimated heart rate and the determined heart rate.

The physiological measurement may comprise a heartbeat and a breathing pattern.

According to a second aspect, there is provided a method comprising supplying an audio signal to a speaker suitable to be applied at a user's ear for rendering the audio signal in the user's ear; acquiring a sound signal by a microphone arranged in vicinity of the speaker to acquire the sound signal from sounds present in the ear of the user; subtracting the audio signal from the sound signal to provide a physiological sound signal; and detecting a physiological measurement from the physiological sound signal.

The method may further comprise filtering the sound signal, the audio signal to be subtracted or the physiological sound signal.

The physiological measurement may comprise a breathing pattern, and the method further may comprise controlling features of an application based on the breathing pattern. The controlling of features of the application may comprise selecting music based on the breathing pattern, wherein the selected music is provided to be comprised in the supplied audio signal. The method may further comprise determining a breathing rate from the breathing pattern. The music may be selected based on the music's beat rate such that the music's beat rate is a monotonic function of the breathing rate.

The method may further comprise selecting music based on the breathing pattern, wherein the selected music is provided to be comprised in the supplied audio signal; and determining a breathing rate from the breathing pattern, wherein the selection of music is based on the music's beat rate such that the music's beat rate is increased until a predetermined breathing rate is reached.

The method may further comprise estimating a heart rate from the breathing pattern. The physiological measurement may comprise a heartbeat, the method may further comprise determining a heartbeat rate from the heartbeat; and comparing the estimated heart rate and the determined heart rate, wherein the result of the comparison is used for controlling the features of the application.

The method may further comprise extracting a heartbeat by low pass filtering the physiological sound signal in a low pass filter to provide a heartbeat signal. The low pass filter may have a cutoff frequency between 3 and 10 Hz, preferably between 3 and 5 Hz, preferably 4 Hz.

The physiological measurement may comprise a heartbeat, and the method may further comprise providing an audio signal which comprises a sub-signal to a second speaker suitable to be applied at the user's other ear, such that the sound signal comprises a signal component emanating from sound provided at the user's other ear and which sound is modulatedly attenuated by pulsating blood of veins of the user when the sound propagates through the head of the user; and detecting the heartbeat from the signal component. The method may further comprise low pass filtering the physiological sound signal in a low pass filter to provide the signal component signal. The low pass filter may have a cutoff frequency between 3 and 10 Hz, preferably between 3 and 5 Hz, preferably 4 Hz.

The physiological measurement may comprise a heartbeat and a breathing pattern.

According to a third aspect, there is provided a computer readable medium comprising program code comprising instructions which when executed by a processor is arranged to cause the processor to perform supplying an audio signal to a speaker suitable to be applied at a user's ear for rendering the audio signal in the user's ear; acquiring a sound signal by a microphone arranged in vicinity of the speaker to acquire the sound signal from sounds present in the ear of the user; subtracting the audio signal from the sound signal to provide a physiological sound signal; and detecting a physiological measurement from the physiological sound signal.

The instructions may further be arranged to cause the processor to select music based on the physiological measurement, wherein the selected music is provided to be comprised in the supplied audio signal.

BRIEF DESCRIPTION OF DRAWINGS

FIG. 1 schematically illustrates an apparatus according to an embodiment.

FIG. 2 is a flow chart illustrating a method according to embodiments.

DETAILED DESCRIPTION

Figure 3:
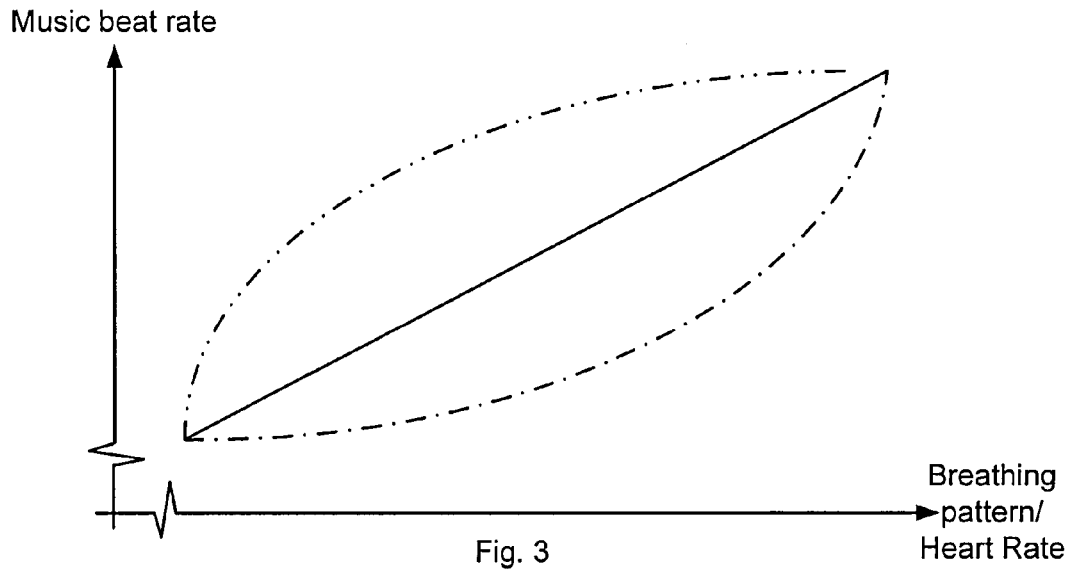
FIG. 3 is a diagram illustrating functions between provided music beat rate and breathing pattern or heart rate.

FIG. 1 schematically illustrates an apparatus 100 according to an embodiment. The apparatus 100 comprises a speaker arrangement 102, e.g. an earphone, which has a speaker 104 and a microphone 106 arranged together with the speaker 104. The speaker 104 is provided with an audio signal, e.g. music, which preferably is provided by an amplifier 108, which in turn may get the audio content from a media player element 109. As will be demonstrated below, the audio signal can also comprise a sub-signal for heartbeat measurements. The microphone 106, which is arranged to acquire heart or breathing sounds and of course the audio sound generated by the speaker 104, provides its output signal to a subtractor 110, which subtracts the audio signal from the microphone signal. Optionally, the microphone signal is filtered by a filter 111a. In addition, or alternatively, the audio sound provided by amplifier 108 may be filtered by a filter 111b before input to subtractor 110. The output from the subtractor 110 essentially comprises a heart and/or breathing sound signal since the signal components emanating from the audio sound are deleted. The heart and/or breathing sound signal is provided to a physiological sound detector 112. Here, it should be noted that a filter 111c can be arranged between the subtractor 110 and the physiological sound detector 112 instead of, or in addition to, the filter 111a between the microphone 106 and the subtractor 112 and/or the filter 111b between the amplifier 108 and the subtractor 110. The breathing sound pattern can for example distinguish between breathing through the nose or the mouth. The breathing sound pattern can alternatively or additionally be a measure on breathing rate, e.g. breaths per minute or period between breaths, duty cycle of inhaling and/or exhaling, etc. From the breathing sound pattern, the physical status of a user can be estimated, e.g. during physical exercising. Similar applies for heart sounds, where heart rate and/or amplitude of heart sound can be determined. The subtractor 110, the optional filter(s) 111a, b, c, and the pattern detector 112 can be part of a signal processor 114 performing the functions of the elements 110, 111(a, b, c), 112, for example in analog or digital domain.

In an embodiment, the breathing pattern can be used for controlling an application 115 such that features of the application are adapted to the breathing pattern and/or the heartbeat.

For example, the application can be a music selection application which selects music with a beat rate that depends on for example the breathing rate. This can for example be neat when listening to music while running or jogging, as breathing is related to the physical effort, and also has a relation to step pace. For example, at running exercise, a 4-4 breathing means inhaling during 4 steps and exhaling during 4 steps, and during different parts of an exercise, different breathing strategies can be used, such as changing to 3-3, 2-2, 2-1 etc. If the music is in pace with breathing and thus steps, the exercise can be improved.

Another example is by determining if breathing is nasal or oral. This can be determined on the different sound characteristics the breathing has when the air is flowing in the head. Nasal breathing can then be taken as a sign of low activity exercising, while oral breathing can be taken as a sign of high activity exercising. Music can then be selected accordingly.

Further another example is by determining if breathing is deep or shallow. This can also be determined from sounds the flowing air is causing in the head, and which sounds can be acquired in the user's ear. An example is to select a lower beat rate on the music if breathing is shallow to calm the user to get into a deep breathing state, which is known to lower heart rate and improve efficiency in exercise. Similarly, if period of breathing is too short to give proper oxygenation in the lungs, lowered music beat rate can improve breathing and exercise.

Still another example is a combination of any of the above breathing patterns, where a proper breathing according to a pre-configured or user-configured model is present, but still showing that pace of the exercise can be increased, and therefore an increased beat rate of the music is selected.

Alternatively, or in combination with any of the examples given above, the heart rate and/or intensity of heartbeat sounds can be used for exercising aid, and optionally in combination with the music selection feature.

Of course, the measured breathing pattern and/or heartbeat can also be used in an exercise aid application without controlling any music selection. Similar, the measured breathing pattern and/or heartbeat can also be used in an application without any connection to exercise aid.

Figure 4:
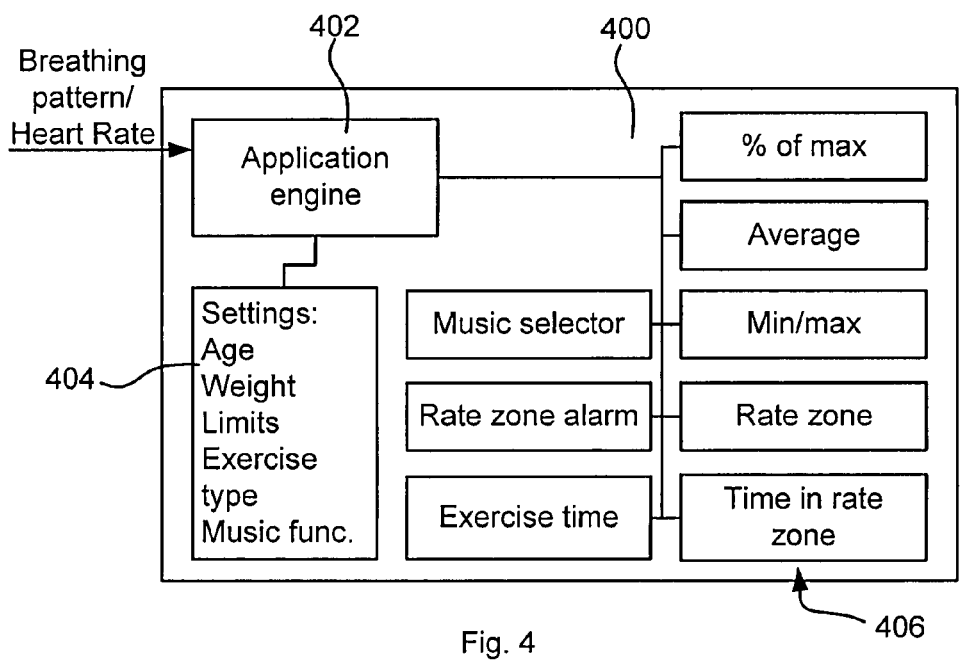
FIG. 4 is a block diagram schematically illustrating an application according to an embodiment.

The application can of course combine other measured or estimated values and their derivatives too, such as step counter, positioning data, altitude, etc. The settings can be pre-defined or user-defined. The settings can also be downloadable from a remote location, e.g. over a wireless communication interface such as a cellular telecommunication system. The measured and estimated values can also be saved in a log for post-exercise analysis. FIG. 4 is a block diagram schematically illustrating an example on objects and features of an exercise enhancing application 400. A breathing pattern signal and/or heartbeat signal is input to the application 400, which is controlled by an application engine 402. The application engine 402 is also enabled to receive settings from a settings object 404, which for example can provide settings made by a user, pre-defined settings, or downloaded setting on age, weight, gender, body mass index, exercise limits, exercise type, music function, etc. to the application engine. The application engine can also control one or more function objects 406 for different features. The application 400 can also control other functions or applications, such as a media player, as demonstrated with reference to FIG. 1. The output interface for this control is preferably controlled by the application engine 402. Here, it should be noted that the example given with reference to FIG. 4 includes a multitude of functions 406. Other examples are any application comprising one or more of the functions given with reference to FIG. 4. The application 400 can for example be implemented as a feature in a mobile phone, a media player, a GPS receiver or a personal digital assistant.

The application can also be independent on physical exercising properties. Breathing can be used for controlling the apparatus 100 on the user's intention, where different breathing patterns are decoded to operation instructions for the apparatus 100, for example changing or pausing music provided by the media player 109.

By nature, the heartbeat produces a weak sound in the head of the user with frequency components mainly corresponding to the heart rate. The heartbeat sound signal acquired by the microphone 106 can be amplified, filtered and processed to produce a heart rate value. The filtering can comprise low-pass filtering, since the heartbeat itself normally is within the range of 0.5 to 3 Hz. Since music content normally is very low at these frequencies, a narrow filter can enhance the heart sound signal significantly.

Alternatively, as shown in FIG. 1, the heartbeat signal is produced by providing a sub-signal via a sub-signal generator 116 to one of the user's ears by a second speaker 118, which can be done together with e.g. music. Preferably, the sub-signal is at a frequency not discernable by the user, e.g. an ultrasonic or a subsonic frequency should be used. As the sound of the sub-signal propagates through the head of the user to the other ear, the heartbeat will modulate, i.e. provide different attenuation, the sub-signal sound through the pulsation of the blood veins. The sound acquired by the microphone 106 in the other ear will comprise the modulated sub-signal sound. A low-pass filter in case of a subsonic sub-signal, and a high-pass filter in case of an ultrasonic sub-signal can be used to suppress the music signal while detecting the heartbeat. By similar signal processing as demonstrated above, the heart rate can be determined. This approach is particularly suitable for stereo earphones.

FIG. 2 is a flow chart illustrating a method according to embodiments, where hashed lines indicate optional actions. The flow chart is for illustrative purposes, and the order of the actions is not to be interpreted as a sequential order. Instead, the actions are preferably to be considered as real-time objects which can be performed in any order, or in parallel. In an audio supply step 200, an audio signal is provided to a speaker suitable for applying in a user's ear, such as an earphone, for rendering of the audio content of the audio signal. In a sound acquisition step 202, sound present in the user's ear is acquired by a microphone arranged together with the speaker. The sound present in the user's ear will be a mix of the rendered audio content and sounds generated in the user's head, such as breathing sounds which emanates from air flows in cavities of the head, and heartbeat sounds from blood pulsating in veins in the head according to any of the examples given with reference to FIG. 1. In an optional sound signal filtering step 203, the acquired sound signal can be filtered to enhance the signal, e.g. attenuating frequencies out of frequency range for breathing sounds and/or heartbeat sounds. In an audio signal subtracting step 204, the audio signal is subtracted from the sound signal to extract a breathing signal. In a physiological sound detection step 206, a breathing pattern and/or heartbeat is detected, as demonstrated with reference to FIG. 1. Optionally, heart rate can be estimated from the detected breathing pattern in a heart rate estimation step 207. Different models for estimating the heart rate from breathing pattern can be used. A user and/or exercise specific model can be used, where one or more characteristics of the breathing pattern are mapped to an expected heart rate. Alternatively, the heart rate can be estimated on the assumption that the faster the breathing rate, the faster the heart rate. Further alternatively, the heart rate can be estimated on the assumption that higher air flow, for example based on the amplitude and/or frequency components of the breathing signal, is mapped to a higher heart rate, and a shallow breathing is mapped to a higher heart rate then deep breathing. The optional heart rate estimation step 207 can be an alternative to the possible heartbeat determination of the physiological sound detection step 206, or a complement for comparison between detected and estimated heart rate, where the comparison can be used as input to an application. In an optional application feature controlling step 209, features of one or more applications can be controlled based on the breathing pattern, alternatively on the estimated heart rate.

FIG. 3 is a diagram illustrating functions between provided music beat rate and breathing pattern or heart rate. For the case of breathing pattern, a determined breathing rate, periodicity, or duty cycle can be used for this type of relation. The solid line illustrates a linear relation between the breathing pattern or estimated heart rate and the music beat rate, while the dot-dashed lines illustrate different non-linear relations. The illustrated lines illustrate monotonic functions for the relation. The application of a monotonic function is particularly suitable when selecting music beat rate from heartbeat rate. Based on breathing pattern, a suitable model out of several non-linear models relating music to heartbeat rate, can be selected. This can further enhance an exercising aid.

Figure 5:
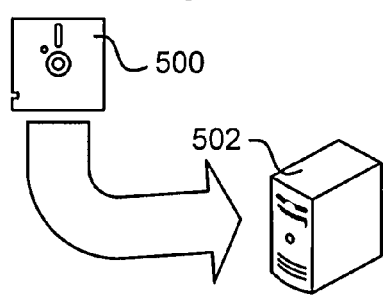
FIG. 5 schematically illustrates a computer readable medium.

The methods according to the present invention are suitable for implementation with aid of processing means, such as computers and/or processors. Therefore, there is provided computer programs, comprising instructions arranged to cause the processing means, processor, or computer to perform the steps of any of the methods according to any of the embodiments described with reference to FIG. 2, in the apparatus. The computer programs preferably comprises program code which is stored on a computer readable medium 500, as illustrated in FIG. 5, which can be loaded and executed by a processing means, processor, or computer 502 to cause it to perform the methods, respectively, according to embodiments of the present invention, preferably as any of the embodiments described with reference to FIG. 2. The computer 502, which can be present in the apparatus as illustrated in FIG. 1, and computer program product 500 can be arranged to execute the program code sequentially where actions of the any of the methods are performed stepwise, or be performed on a real-time basis, where actions are taken upon need and availability of needed input data. The processing means, processor, or computer 502 is preferably what normally is referred to as an embedded system. Thus, the depicted computer readable medium 500 and computer 502 in FIG. 5 should be construed to be for illustrative purposes only to provide understanding of the principle, and not to be construed as any direct illustration of the elements.

The invention claimed is:

1. An apparatus comprising
a media player element configured to provide audio content for rendering;
a speaker suitable to be applied at a user's ear and enabled to be supplied with an electronic audio signal for rendering, the electronic audio signal being generated based on the audio content provided by the media player element;
a microphone arranged in vicinity of the speaker to acquire a sound signal from sounds present in the ear of the user, the acquired sounds including audio sound generated by the speaker for rendering the audio content; and
a signal processor, wherein the signal processor has a first input and a second input, the second input of the signal processor being coupled to the microphone, wherein the first input of the signal processor is different from the second input and is coupled to an input of the speaker at which the electronic audio signal is supplied to the speaker, and the signal processor is arranged to filter the acquired sound signal and to then subtract the electronic audio signal which is supplied to the speaker for rendering and which is received at the first input of the signal processor from the filtered acquired sound signal to provide a physiological sound signal, and the signal processor is further arranged to detect a physiological measurement from the physiological sound signal.

2. The apparatus according to claim 1, further comprising a filter arranged to filter the sound signal, the audio signal to be subtracted or the physiological sound signal.

3. The apparatus according to claim 1, further comprising an application arranged to control features of the application based on the physiological measurement.

4. The apparatus according to claim 3, wherein the application is arranged to make a music selection based on the physiological measurement, wherein the selected music is comprised in the supplied audio signal.

5. The apparatus according to claim 4, wherein the physiological measurement comprises a breathing pattern.

6. The apparatus according to claim 5, wherein the signal processor is arranged to determine a breathing rate from the breathing pattern.

7. The apparatus according to claim 6, wherein the music is selected based on the music's beat rate, the music's beat rate of the selected music being a monotonic function of the breathing rate.

8. The apparatus according to claim 6, wherein the music is selected based on the music's beat rate, the music's beat rate of the selected music being a function of the breathing rate wherein the music's beat rate is increased until a predetermined breathing rate is reached.

9. The apparatus according to claim 4, wherein the physiological measurement comprises a heartbeat.

10. The apparatus according to claim 9, wherein the signal processor is arranged to determine a heartbeat rate from the heartbeat.

11. The apparatus according to claim 10, wherein the music is selected based on the music's beat rate, the music's beat rate of the selected music being a monotonic function of the heartbeat rate.

12. The apparatus according to claim 10, wherein the music is selected based on the music's beat rate, the music's beat rate of the selected music being a function of the heartbeat rate wherein the music's beat rate is increased until a predetermined heartbeat rate is reached.

13. The apparatus according to claim 9, wherein the signal processor is arranged to extract the heartbeat by low pass filtering the physiological sound signal in a low pass filter to provide a heartbeat signal.

14. The apparatus according to claim 13, wherein the low pass filter has a cutoff frequency between 3 and 10 Hz.

15. The apparatus according to claim 9, further comprising a second speaker suitable to be provided at the user's other ear, wherein an audio signal provided to the second speaker comprises a sub-signal and wherein the sound signal comprises a signal component emanating from sound provided at the user's other ear and which sound is modulatedly attenuated by pulsating blood of veins of the user when the sound propagates through the head of the user, and the heartbeat is extractable from the signal component.

16. The apparatus according to claim 15, wherein the signal processor is arranged to extract the heartbeat by low pass filtering the physiological sound signal in a low pass filter to provide the signal component signal.

17. The apparatus according to claim 16, wherein the low pass filter has a cutoff frequency between 3 and 10 Hz.

18. The apparatus according to claim 5, comprising a heart rate estimator arranged to estimate heart rate from the breathing pattern.

19. The apparatus according to claim 18, wherein the physiological measurement comprises a heartbeat, the signal processor is arranged to determine a heartbeat rate from the heartbeat, and the apparatus is further arranged to provide a comparison between the estimated heart rate and the determined heart rate.

20. The apparatus according to claim 1, wherein the physiological measurement comprises a heartbeat and a breathing pattern.

21. A method comprising
providing, by a media player element, audio content for rendering;
supplying an electronic audio signal to a speaker suitable to be applied at a user's ear for rendering the audio signal in the user's ear, the electronic audio signal being generated based on the audio content provided by the media player element;
acquiring a sound signal by a microphone arranged in vicinity of the speaker to acquire the sound signal from sounds present in the ear of the user, the acquired sounds including audio sound generated by the speaker for rendering the audio content, the acquired sounds being received by a signal processor which has a first input and a second input, the acquired sounds being received at the second input of the signal processor, and the first input of the signal processor being different from the second input and being coupled to an input of the speaker;

monitoring, by the signal processor, the electronic audio signal supplied to the speaker for rendering;

filtering the acquired sound signal;

subtracting the monitored electronic audio signal which is supplied to the speaker for rendering from the filtered acquired sound signal to provide a physiological sound signal; and detecting a physiological measurement from the physiological sound signal.

22. The method according to claim 21, further comprising filtering the sound signal, the audio signal to be subtracted or the physiological sound signal.

23. The method according to claim 21, wherein the physiological measurement comprises a breathing pattern, and the method further comprising controlling features of an application based on the breathing pattern.

24. The method according to claim 23, wherein the controlling of features of the application comprises selecting music based on the breathing pattern, wherein the selected music is provided to be comprised in the supplied audio signal.

25. The method according to claim 24, further comprising determining a breathing rate from the breathing pattern.

26. The method according to claim 25, wherein the music is selected based on the music's beat rate, the music's beat rate of the selected music being a monotonic function of the breathing rate.

27. The method according to claim 23, further comprising
selecting music based on the breathing pattern, wherein the selected music is provided to be comprised in the supplied audio signal; and
determining a breathing rate from the breathing pattern, wherein the selection of music is based on the music's beat rate, the music's beat rate of the selected music being increased until a predetermined breathing rate is reached.

28. The method according to claim 23, further comprising estimating a heart rate from the breathing pattern.

29. The method according to claim 28, wherein the physiological measurement comprises a heartbeat, the method further comprising determining a heartbeat rate from the heartbeat; and comparing the estimated heart rate and the determined heart rate, wherein the result of the comparison is used for controlling the features of the application.

30. The method according to claim 21, further comprising extracting a heartbeat by low pass filtering the physiological sound signal in a low pass filter to provide a heartbeat signal.

31. The method according to claim 30, wherein the low pass filter has a cutoff frequency between 3 and 10 Hz.

32. The method according to claim 21, wherein the physiological measurement comprises a heartbeat, and the method further comprises providing an audio signal which comprises a sub-signal to a second speaker suitable to be applied at the user's other ear, wherein the sound signal comprises a signal component emanating from sound provided at the user's other ear and which sound is modulatedly attenuated by pulsating blood of veins of the user when the sound propagates through the head of the user; and detecting the heartbeat from the signal component.

33. The method according to claim 32, further comprising low pass filtering the physiological sound signal in a low pass filter to provide the signal component signal.

34. The method according to claim 33, wherein the low pass filter has a cutoff frequency between 3 and 10 Hz.

35. The method according to claim 21, wherein the physiological measurement comprises a heartbeat and a breathing pattern.

36. A non-transitory computer readable medium comprising program code comprising instructions which when executed by a processor is arranged to cause the processor to perform providing, by a media player element, audio content for rendering;

supplying an electronic audio signal to a speaker suitable to be applied at a user's ear for rendering the audio signal in the user's ear, the electronic audio signal being generated based on the audio content provided by the media player element;

acquiring a sound signal by a microphone arranged in vicinity of the speaker to acquire the sound signal from sounds present in the ear of the user, the acquired sounds including audio sound generated by the speaker for rendering the audio content, the acquired sounds being received by a signal processor which has a first input and a second input, the acquired sounds being received at the second input of the signal processor, and the first input of the signal processor being different from the second input and being coupled to an input of the speaker;

monitoring, by the signal processor, the electronic audio signal supplied to the speaker;

filtering the acquired sound signal;

subtracting the monitored electronic audio signal which is supplied to the speaker for rendering from the filtered acquired sound signal to provide a physiological sound signal; and detecting a physiological measurement from the physiological sound signal.

37. The computer readable medium according to claim 36, wherein the instructions are further arranged to cause the processor to select music based on the physiological measurement, wherein the selected music is provided to be comprised in the supplied audio signal.

* * * * *